United States Patent
Osborne

(10) Patent No.: US 9,727,811 B2
(45) Date of Patent: Aug. 8, 2017

(54) METHODS AND APPARATUS FOR BARCODE READING AND ENCODING

(71) Applicant: Samsung Pay, Inc., Burlington, MA (US)

(72) Inventor: John Osborne, Incline Village, NV (US)

(73) Assignee: Samsung Pay, Inc., Burlington, MA (US)

( * ) Notice: Subject to any disclaimer, the term of this patent is extended or adjusted under 35 U.S.C. 154(b) by 0 days.

(21) Appl. No.: 14/743,363

(22) Filed: Jun. 18, 2015

(65) Prior Publication Data

US 2015/0371128 A1   Dec. 24, 2015

Related U.S. Application Data

(60) Provisional application No. 62/014,592, filed on Jun. 19, 2014.

(51) Int. Cl.
| | | |
|---|---|---|
| *G06K 7/10* | (2006.01) | |
| *G06K 19/06* | (2006.01) | |
| *G06K 7/14* | (2006.01) | |
| *A61K 8/27* | (2006.01) | |
| *A61K 8/34* | (2006.01) | |
| *A61K 8/37* | (2006.01) | |
| *A61Q 17/04* | (2006.01) | |
| *A61Q 19/00* | (2006.01) | |
| *A61K 8/92* | (2006.01) | |
| *A61K 8/97* | (2017.01) | |

(52) U.S. Cl.
CPC ......... *G06K 19/06112* (2013.01); *A61K 8/27* (2013.01); *A61K 8/34* (2013.01); *A61K 8/37* (2013.01); *A61K 8/92* (2013.01); *A61K 8/97* (2013.01); *A61Q 17/04* (2013.01); *A61Q 19/00* (2013.01); *G06K 7/1413* (2013.01)

(58) Field of Classification Search
CPC ..................... G06K 19/06112; G06K 7/1413
USPC .................................................. 235/462.01
See application file for complete search history.

(56) References Cited

U.S. PATENT DOCUMENTS

| | | | | |
|---|---|---|---|---|
| 5,243,655 | A * | 9/1993 | Wang | G06F 3/002 |
| | | | | 235/462.09 |
| 8,342,406 | B2 * | 1/2013 | Saunders | G06K 7/1095 |
| | | | | 235/462.01 |
| 9,098,498 | B2 * | 8/2015 | Alexeev | G06Q 20/32 |
| 2010/0078472 | A1 * | 4/2010 | Lin | G06Q 20/32 |
| | | | | 235/379 |

(Continued)

OTHER PUBLICATIONS

International Search Report and Written Opinion, for International PCT Patent Application No. PCT/US15/36488, dated Sep. 17, 2015, pp. 1-7.

*Primary Examiner* — Seung Lee
(74) *Attorney, Agent, or Firm* — Seyfarth Shaw LLP; Brian Michaelis

(57) ABSTRACT

The present invention is directed towards methods and apparatus for barcode reading and encoding. In accordance with an embodiment, a method of reading and encoding barcode information is provided. A one-dimensional barcode image is decoded using an electronic device to obtain data encoded by the one-dimensional barcode image. The data is encoded into a two-dimensional barcode image. The two-dimensional barcode image is displayed in a manner suitable for reading by a scanner configured for reading two-dimensional barcodes.

25 Claims, 3 Drawing Sheets

(56) References Cited

U.S. PATENT DOCUMENTS

| | | |
|---|---|---|
| 2011/0084141 A1 | 4/2011 | Napper et al. |
| 2012/0029994 A1* | 2/2012 | Barkan .............. G06Q 30/0207 |
| | | 705/14.25 |
| 2013/0344853 A1 | 12/2013 | Lee et al. |
| 2014/0054367 A1 | 2/2014 | Alexeev |

* cited by examiner

METHODS AND APPARATUS FOR BARCODE READING AND ENCODING

BACKGROUND OF THE INVENTION

This invention relates generally to reading and encoding barcodes.

A barcode is a machine-readable representation of data. Originally, barcodes represented data by a series of parallel lines (or "bars") having varying widths and spacing. Such barcodes are referred to as one-dimensional (1D) barcodes. Universal product code (UPC) is a widely-used type of 1D barcode. Barcodes have since evolved to include two-dimensional (2D) barcodes in which data is represented by a two-dimensional geometric pattern. While 2D barcodes use a variety of symbols other than bars, they are also referred to as barcodes. Quick response (QR) code is a widely-used type of 2D barcode.

Barcodes are typically printed on items, such as paper labels or packaging for goods, manufacturer's or retailer's coupons, or on tickets or passes, such as airline boarding passes, or on advertisements for products and services. Barcode scanners (also referred to as barcode readers) are used to extract information from barcodes. Barcode scanners are found in many different types of facilities including stores and supermarkets, airport security check-in and boarding areas, stadiums, libraries, test centers, conference centers, and in many other contexts. The use of barcodes and barcode scanners has dramatically increased the speed and convenience of performing many commonplace transactions.

Due to differences in the characteristics of different types of barcodes, a scanner designed for reading one type of barcode may not be able to reliably read another type of barcode, if it can read them at all.

SUMMARY OF THE INVENTION

The present invention is directed towards methods and apparatus for barcode reading and encoding. In accordance with an embodiment, a method of reading and encoding barcode information is provided. A one-dimensional barcode image is decoded using an electronic device to obtain data encoded by the one-dimensional barcode image. The data is encoded into a two-dimensional barcode image. The two-dimensional barcode image is displayed in a manner suitable for reading by a scanner configured for reading two-dimensional barcodes. In accordance with another embodiment, an apparatus for reading and encoding barcode information is provided. The apparatus comprises an electronic device configured to decode a one-dimensional barcode image to obtain data encoded by the one-dimensional barcode image. The electronic device is further configured to encode the data into a two-dimensional barcode image and to display the two-dimensional barcode image in a manner suitable for reading by a scanner configured for reading two-dimensional barcodes. These and other embodiments are described in more detail herein.

BRIEF DESCRIPTION OF THE DRAWINGS

The present invention is described with respect to particular exemplary embodiments thereof and reference is accordingly made to the drawings in which.

DETAILED DESCRIPTION OF A PREFERRED EMBODIMENT OF THE INVENTION

One-dimensional (1D) barcodes are used in many different encoding schemes. 1D barcode types include, but are not limited to: UPC, UPC-A, GTIN-12, UPC-E, CODE39, CODE39 Extended, Code128, GS1-128, EAN-128, UCC-128, EAN-13, GTTIN-13, EAN, EAN-8, GTIN-8, ISBN-13, ISSN, ISMN, EAN-14, GTIN-14, DUN-14, SCC-14, ITF-14, EAN-18/NVE, SSCC-18, Code 25, Code25 Interleaved, JAN, EAN-5, EAN-2, EAN-99, EAN-Velocity, ISBN-13, ISBN-10, Codabar, Code 93, Code 93 Extended, PZN7, PZN8, Leticode, Identicode, Code 128A, Code 128B, Code 128C, MSI Plessey, PostNet, and Royal Mail. Two-dimensional (2D) barcode types include, but are not limited to: Aztec, QR codes, Micro QR code, stacked barcode, PDF417, Truncated PDF417, Micro PDF417, ShotCode, High Capacity Color Barcode (HCCB), MaxiCode, EZcode, Codablock, Code 16K, Code 49, DataMatrix, GS1 Composite, and GS1 Databar. In comparison to 1D barcodes, 2D barcodes tend to be more compact and capable of carrying more bits of data in their commonly used forms.

Point of Sale (POS) systems and other barcode scanning systems may have a 1D or 2D scanner, but they seldom have both. Barcode scanners designed specifically for reading 1D barcodes (referred to herein as 1D scanners) are generally incapable of reading 2D barcodes, although scanners specifically designed for reading 2D barcodes (referred to herein as 2D scanners) are in some instances capable of imaging 1D barcodes. Even where a 2D scanner is capable of reading 1D barcodes, due to angle of rotation, misregistration, and distance from the imager, 2D scanners may fail to successfully decode a 1D barcode image. A low rate of successful scans tends to result in reduced throughput and productivity, as well as delays and introduction of human error into the POS transaction or other type of transaction involving a barcode.

Embodiments of the present invention are directed towards systems and methods for converting 1D barcode images into 2D barcode images so that high rates of successful 1D barcode reading may be achieved with a 2D scanner. Information obtained from the 1D barcode is encoded into a 2D barcode image which is then scanned. Redundant information may optionally also be encoded into the 2D barcode image so as to further improve rates of successful barcode reading.

Figure 1A:
FIGS. 1A-E illustrate several cases of how 1D barcodes can be misread.
Figure 1B:

FIGS. 1A-E illustrate several cases of how 1D barcodes might be misread. In FIGS. 1A-E, several examples of problematic 1D barcodes as interpreted by 2D scanners are displayed. In FIG. 1A, a normal barcode image is presented. In FIG. 1B, a barcode is angled, as if the imaging device did not align correctly with the original barcode. In 1D scanners, the first few lines allow the scanner to easily compensate for such rotations, as each line will be skewed by the same percentage dependent on the angle of rotation. In 2D barcode imagers, however, pixellation occurs where the line positions are interpreted from discrete pixels, and additional error is introduced into the determination of the width of the line.

Figure 1C:
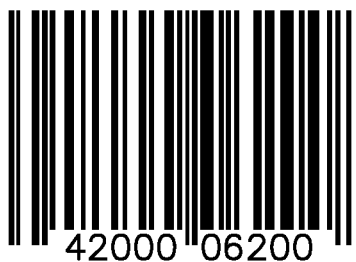
Figure 1D:
Figure 1E:

In FIG. 1C, a misregistration has occurred, such that the last few lines of the original 1D barcode are not visible to the scanner. This will result in the scanner not being able to correctly decode the image. In FIG. 1D, both misalignment and misregistration are depicted. 2D dimensional markers are important in making the image scan successful, whereas 1D barcodes do not have such a robust a mechanism. In FIG. 1E, the barcode image is scaled too small. In a 2D scanner, the distance from the scanner to the 1D barcode image is important, as is as the original size of the 1D barcode. Again because of pixellation, if the image is scaled too small, errors due to pixel conversion increase.

Figure 2:
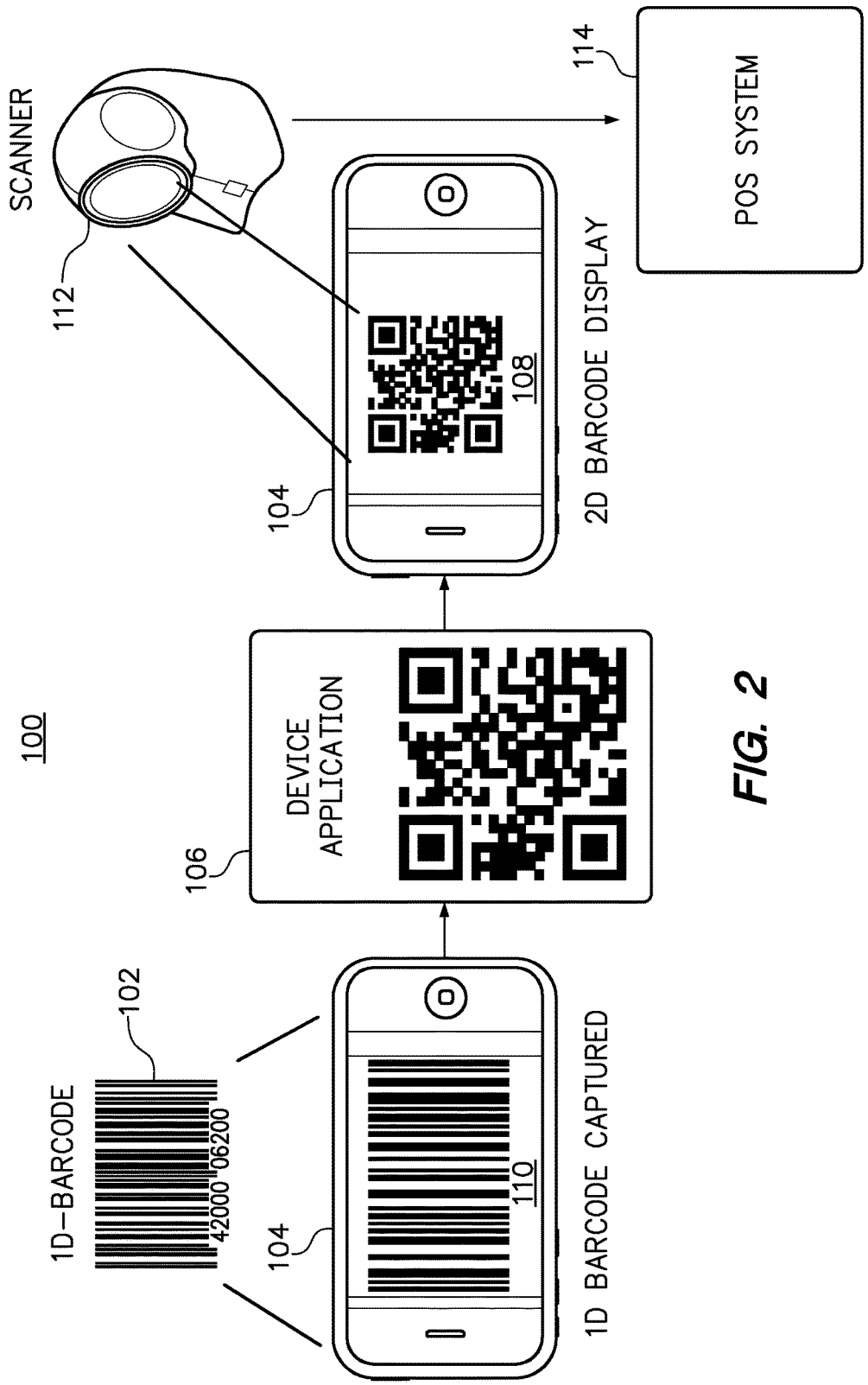
FIG. 2 illustrates a system for scanning a 1D barcode, converting the 1D barcode to a 2D barcode and presenting the 2D code to a scanner in accordance with an embodiment of the present invention.

FIG. 2 illustrates a system 100 for scanning a 1D barcode, converting the 1D barcode to a 2D barcode and presenting the 2D code to a scanner in accordance with an embodiment of the present invention. As shown in FIG. 1, a 1D barcode 102 exists on some medium than can be scanned or imaged. For example, the 1D barcode 102 may be printed on a paper label, product packaging, boarding pass or other medium. Alternatively, the 1D barcode 102 may be displayed on a display screen of an electronic device. The 1D barcode 102 can be encoded such that it represents any number of bits of information, but typically such 1D barcodes contain two to 128 bits of numeric information and, in the case of common codes, such 1D barcodes contains approximately 12 bits of numeric information.

The barcode 102 may be scanned by a scanning device 104. The 1D barcode 102 is then converted by the scanning device 104 into the unique numeric value represented by the 1D barcode 102.

In an embodiment, the 1D barcode 102 is captured by a mobile device 104 taking a photographic image of the 1D barcode and processing the photographic image to determine the data content encoded therein. In an alternative embodiment, the scanning device 104 includes a light source that emits light to be reflected from the 1D barcode image and a light sensor that translates optical impulses reflected from the barcode into electrical signals as well as decoder circuitry that analyzes the signals provided by the sensor to determine the barcode's content.

In an embodiment, a software application 106 operating on the scanning device is employed to capture and decode the 1D barcode 102 to obtain a numeric value and to translate the numeric value into a 2D barcode image 108 that represents the unique numeric value obtained from the 1D barcode 102. The application 106 can be initiated by a user of the device 104. For example, the user may select the application 106 from among a plurality of applications present on the device 104. The user may also use the device 104 to obtain a photographic image of the 1D barcode 102. A captured 1D barcode image 110 may be displayed on a display screen of the device 104, as shown in FIG. 1, so that the user can visually confirm that the capture was successfully completed.

In the case where the 1D barcode 102 is captured by a mobile device 104 taking a photographic image of the 1D barcode, the application 106 may then process the image data representing the captured 1D barcode to determine its type and to retrieve the data encoded therein. Once the data is obtained, the same application 106 or a different application may be employed to encode the data retrieved from the 1D barcode 102 into the 2D barcode image 108, and may also include additional information, which can include redundant information.

In an embodiment, the application 106 may have a default type of 2D code specified and allow the user to select a different type of encoding either temporarily (for this transaction only) or for all subsequent transactions.

The device 104 includes 1D scanner functionality and is also preferably equipped with a display (e.g. an LCD display screen) that is capable of displaying the resulting 2D barcode image 108 such that it can be scanned by a 2D scanner 112. In addition to the display, or as an alternative to the display, the device 104 may be equipped with a printing device that is capable of printing the 2D barcode image onto a medium, such as paper, that can be scanned by a 2D scanner 112.

The device 104 may be a standalone unit, or other type of device or system that is capable of reading a 1D code and producing a 2D barcode on an electronic display screen, paper or some other medium. Suitable device types may include, but are not limited to: PDAs, mobile phones or other mobile devices, tablet computers, laptop computers, paper printers, badge printers, ticket printers, electronic paper, OLED displays, LCD displays, or LED matrix displays. Devices that can be employed as a 1D scanner may include, but are not limited to: a conventional barcode reader such as pen style reader, keyboard wedge, laser reader, or another imager such as mobile device camera. The device 104 may include dedicated hardware and may function as a standalone barcode reader, or the device may include general-purpose hardware, such as that of a mobile phone or tablet, and appropriate application software that controls the hardware to perform the function of scanning and decoding the 1D barcode. In an embodiment, the device 104 that performs the scanning of the 1D barcode and translation of the 1D barcode to a 2D barcode is a mobile phone.

The device 104 and/or the application 106 preferably convert the data from the 1D barcode into a 2D representation 108 containing the same data. The 2D barcode can be any 2D barcode type, including any of standard 2D barcode types. Depending on the device 104 and the 2D scanning system targeted, other proprietary or new encoding schemes could be used.

In an embodiment, the 2D barcode 108 is encoded so as to include multiple redundant copies of the same information, such that the redundant information can be used for detecting or correcting errors. Alternatively, or in in addition to inclusion of multiple copies of the information, some 2D barcode encoding schemes employ error correcting codes (ECC) that can employed to increase the successful read rate of the embedded 1D barcode data. In addition, any form of ECC, FireCode, or redundant information could be employed to enhance the read rate of the code, as 2D barcodes tend to have significantly more data space than 1D barcodes. For example, the unique numeric value represented by the 1D barcode 102 could be encoded in accordance with an ECC prior to encoding the value into the 2D barcode. Upon decoding the 2D barcode, the value obtained from the 2D barcode can be further decoded in accordance with the ECC in order to reconstruct the original unique numeric value represented by the 1D barcode 102.

In other embodiments, if Internet access or another communication medium is available to the device 104, the barcode information obtained from the 1D barcode 102 may be used as a lookup key with a third party or other local or remote device or service to obtain additional information to be encoded into the 2D barcode image 108. For example, the device 104 may have access to the Internet or some other storage medium for information such as, but not limited to, an internal database, SD card, external drive, or network (e.g. LAN), additional information can be obtained that can be included in the encoded 2D barcode image. This data can include additional discounts, routing information for a POS system, other Internet URLs, or information to be displayed to the user by the application 106.

The resulting 2D barcode 108 is displayed by the device 104 or printed to a medium and then presented to the 2D scanner 112. A POS system 114 or other type of barcode processing system may then receive and decode the 2D barcode to retrieve the information encoded into the original 1D barcode. This data is then used by the POS system 114 to either initiate a transaction (in the case where the 1D data was an inventory item), or deduct from the transaction if the 1D barcode were a coupon or other value document. The system 114 can be a conventional POS system which may or may not require modification to its hardware and/or its software to be capable of reading the 2D code and interpreting it as a 1D barcode, for example, for redemption or inventory.

Figure 3:
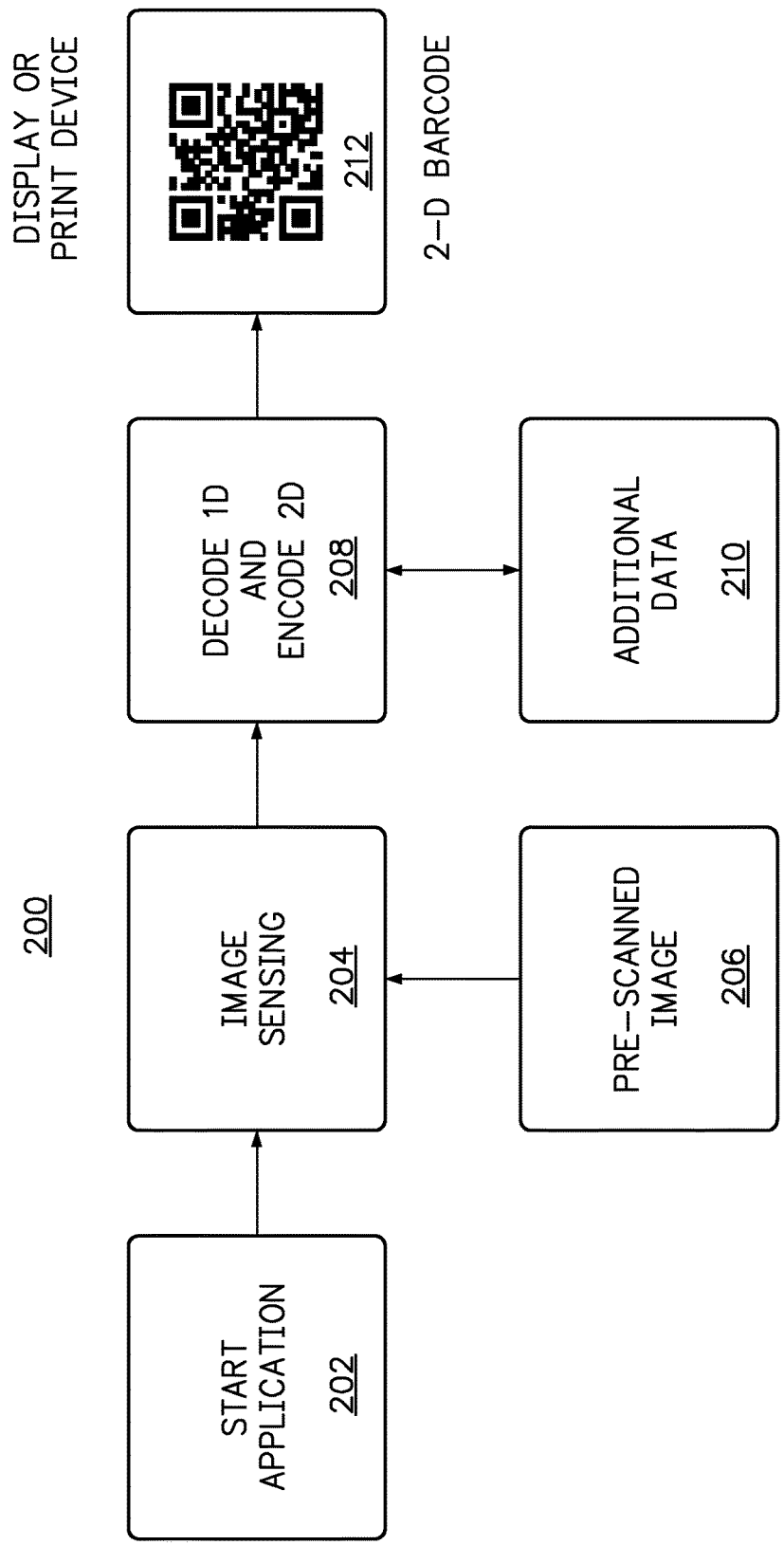
FIG. 3 depicts a flow diagram of an example application in a mobile device or tablet in accordance with an embodiment of the present invention.

FIG. 3 depicts a flow diagram 200 of an example application in a mobile device or tablet in accordance with an embodiment of the present invention. The application may be stored in a machine-readable storage medium within the device. The application may be configured to be running in the device whenever the device is powered on, for example in a dedicated device. Alternatively, the device may be a general-purpose computing device, such as a mobile smart phone, in which the user selects the application to run 100. For example, the application 106 shown in FIG. 2 can operate on the device 104 which is also shown in FIG. 2 in accordance with the flow diagram 300 of FIG. 3.

The application may begin operation in a step 202. In a step 204, the application enables an image sensor of the device 104 so the device 104 captures an image of the 1D barcode. In a step 206, which can be an alternative to step 204, the image can be obtained by the camera application from another source. For example, the image may be a pre-scanned image obtained from a data storage medium of the device 104, or the image can be obtained by the device 104 from a remote location, such as via email or otherwise electronically communicated to the device 104. In such a case, the application preferably allows the user to select a pre-existing image in step 206 as an alternative to initiating image capture in step 204.

Once the image is captured or selected in step 204 or 206, the image is processed in step 206 by the application to decode the 1D barcode image and then encode the 2D barcode image, as described herein. In a step 210, additional information to be encoded into the 2D barcode image may be obtained, as described herein.

In a step 212, a 2D barcode can be displayed for scanning by a 2D scanner. In other embodiments, the 2D barcode image can be printed to some convenient medium or stored on the device for later use.

The foregoing detailed description of the present invention is provided for the purposes of illustration and is not intended to be exhaustive or to limit the invention to the embodiments disclosed. Accordingly, the scope of the present invention is defined by the appended claims.

What is claimed is:

1. A method of reading and encoding barcode information comprising steps of:
   decoding a one-dimensional barcode image using an electronic device to obtain data encoded by the one-dimensional barcode image wherein the electronic device comprises a scanning device having a light source and a light sensor that translates optical impulses reflected from the one-dimensional barcode image into electrical signals and wherein said decoding comprises the electronic device processing the electrical signals to obtain the data encoded by the one-dimensional barcode image;
   encoding the data into a two-dimensional barcode image, the resulting two-dimensional barcode image containing encoded data obtained from the one-dimensional barcode and no other barcode, wherein said encoding the data into the two-dimensional barcode image further comprises encoding data that is redundant of the data obtained from the one-dimensional barcode image into the two-dimensional barcode image; and
   displaying the two-dimensional barcode image in a manner suitable for reading by a scanner configured for reading two-dimensional barcodes.

2. The method according to claim 1, further comprising displaying the one-dimensional barcode image on a display screen of the electronic device.

3. The method according to claim 1, wherein said displaying the two-dimensional barcode image comprises displaying the two-dimensional barcode image on a display screen of the electronic device.

4. The method according to claim 1, wherein said displaying the two-dimensional barcode image comprises printing the two-dimensional barcode image onto a medium that can be scanned by a scanner configured for reading two-dimensional barcodes.

5. The method according to claim 1, wherein in said encoding step multiple redundant copies of the data obtained from the one-dimensional barcode image are encoded into the two-dimensional barcode image.

6. The method according to claim 5, wherein the redundant data comprises multiple copies of the same data obtained from the one-dimensional barcode image.

7. The method according to claim 5, wherein said encoding data that is redundant of the data obtained from the one-dimensional barcode image into the two-dimensional barcode image further comprises employing error correction coding.

8. The method according to claim 1, wherein data encoded by the one-dimensional barcode image is used as a lookup key with a third party or other local or remote device or service to obtain additional information to be encoded into the two-dimensional barcode image.

9. The method according to claim 1, wherein the redundant data comprises one copy of the data obtained from the one-dimensional barcode image.

10. An apparatus for reading and encoding barcode information comprising an electronic device configured to decode one-dimensional barcode image to obtain data encoded by the one-dimensional barcode image wherein the electronic device comprises a scanning device having a light source and a light sensor that translates optical impulses reflected from the one-dimensional barcode image into electrical signals and wherein said decoding comprises the electronic device processing the electrical signals to obtain the data encoded by the one-dimensional barcode image and wherein the electronic device is further configured to encode the data into a two-dimensional barcode image, the resulting two-dimensional barcode image containing encoded data obtained from the one-dimensional barcode and no other barcode, wherein said encoded data in the two-dimensional barcode image further comprises redundant data obtained from the one-dimensional barcode image, and the electronic device being further configured to display the two-dimensional barcode image in a manner suitable for reading by a scanner configured for reading two-dimensional barcodes.

11. The apparatus according to claim 10, wherein the electronic device further comprises a display screen that displays the one-dimensional barcode image.

12. The apparatus according to claim 10, wherein the electronic device further comprises a display screen that displays the two-dimensional barcode image.

13. The apparatus according to claim 10, wherein the two-dimensional barcode image is printed onto a medium that can be scanned by a scanner configured for reading two-dimensional barcodes.

14. The apparatus according to claim 10, wherein the electronic device is further configured to encode multiple redundant copies of the data obtained from the one-dimensional barcode image into the two-dimensional barcode image.

15. The apparatus according to claim 14, wherein the redundant data comprises multiple copies of the same data obtained from the one-dimensional barcode image.

16. The apparatus according to claim 14, wherein the redundant data is encoded into the two-dimensional barcode image by employing error correction coding.

17. The apparatus according to claim 10, wherein data encoded by the one-dimensional barcode image is used as a lookup key with a third party or other local or remote device or service to obtain additional information to be encoded into the two-dimensional barcode image.

18. The apparatus according to claim 10, wherein the redundant data comprises one copy of the data obtained from the one-dimensional barcode image.

19. A method of reading and encoding barcode information comprising steps of:
   decoding a one-dimensional barcode image using an electronic device to obtain data encoded by the one-dimensional barcode image;
   encoding the data into a two-dimensional barcode image, wherein data encoded by the one-dimensional barcode image is used as a lookup key with a third party or other local or remote device or service to obtain additional information to be encoded into the two-dimensional barcode image and wherein the resulting two-dimensional barcode image contains encoded data obtained from the one-dimensional barcode and no other barcode, wherein said encoded data in the two-dimensional barcode image further comprises redundant data obtained from the one-dimensional barcode image; and
   displaying the two-dimensional barcode image in a manner suitable for reading by a scanner configured for reading two-dimensional barcodes.

20. The method according to claim 17, wherein a photographic image of the one-dimensional barcode is obtained by the electronic device and wherein said decoding comprises the electronic device processing the image data to obtain the data encoded by the one-dimensional barcode image.

21. The method according to claim 17, wherein the electronic device comprises a scanning device having a light source and a light sensor that translates optical impulses reflected from the one-dimensional barcode image into electrical signals and wherein said decoding comprises the electronic device processing the electrical signals to obtain the data encoded by the one-dimensional barcode image.

22. The method according to claim 19, wherein in said encoding step multiple redundant copies of the data obtained from the one-dimensional barcode image are encoded into the two-dimensional barcode image.

23. The method according to claim 22, wherein the redundant data comprises multiple copies of the same data obtained from the one-dimensional barcode image.

24. The method according to claim 19, wherein said encoding data into the two-dimensional barcode image further comprises employing error correction coding.

25. The method according to claim 19, wherein the redundant data comprises one copy of the data obtained from the one-dimensional barcode image.

\* \* \* \* \*